United States Patent [19]

Evans et al.

[11] Patent Number: 5,206,414

[45] Date of Patent: Apr. 27, 1993

[54] PROCESS FOR THE PREPARATION OF HYDROXYPHENYLPROPIONIC ACID ESTERS

[75] Inventors: Samuel Evans; Paul Dubs, both of Marly; Milos Rusek, Binnigen; Zdenek Mazour, Lausen; Arpad Major, Kaisten, all of Switzerland

[73] Assignee: Ciba-Geigy Corporation, Ardsley, N.Y.

[21] Appl. No.: 876,813

[22] Filed: Apr. 29, 1992

Related U.S. Application Data

[63] Continuation of Ser. No. 639,466, Jan. 10, 1991, abandoned.

[30] Foreign Application Priority Data

Jan. 11, 1990 [CH] Switzerland ............................. 86/90
Jan. 11, 1990 [CH] Switzerland ............................. 87/90

[51] Int. Cl.$^5$ .......................................... C07C 69/76
[52] U.S. Cl. .................................... 560/75; 546/218; 546/226; 549/465; 549/478
[58] Field of Search ................. 560/75; 546/218, 226; 549/465, 478

[56] References Cited

U.S. PATENT DOCUMENTS

| | | |
|---|---|---|
| 3,247,240 | 4/1966 | Meier et al. |
| 3,285,855 | 11/1966 | Dexter et al. |
| 3,364,250 | 1/1968 | Dexter et al. |
| 3,644,482 | 2/1972 | Dexter et al. |
| 3,840,585 | 10/1974 | Yamada et al. |
| 4,228,297 | 10/1980 | Haeberli et al. |
| 4,536,593 | 8/1985 | Orban et al. |
| 4,659,863 | 4/1987 | Burton |

FOREIGN PATENT DOCUMENTS

| | | |
|---|---|---|
| 0066189 | 12/1982 | European Pat. Off. |
| 2364121 | 7/1974 | Fed. Rep. of Germany |
| 2364126 | 7/1974 | Fed. Rep. of Germany |

OTHER PUBLICATIONS

Derwent Abst. 87-105824/15.

*Primary Examiner*—Paul J. Killos
*Attorney, Agent, or Firm*—Luther A. R. Hall

[57] ABSTRACT

A process for the preparation of compounds of the general formula

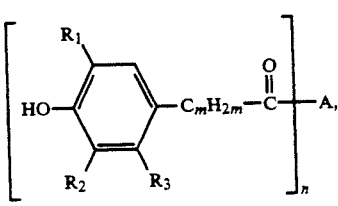

where
$R_1$ and $R_2$ are identical or different and are hydrogen, $C_1$-$C_{18}$alkyl, phenyl, $C_1$-$C_4$alkyl-substituted phenyl, $C_7$-$C_9$phenylalkyl, $C_5$-$C_{12}$cycloalkyl or $C_1$-$C_4$alkyl-substituted $C_5$-$C_{12}$cycloalkyl,
$R_3$ is hydrogen or methyl,
m is 0, 1, 2 or 3, and
n is a number from 1 to 4 or 6, and
A is as defined in the description,
by reacting a compound of the formula II

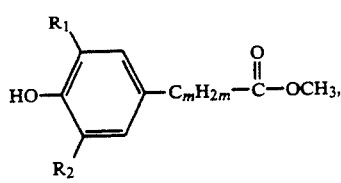

where m, $R_1$ and $R_2$ are as defined above, with a compound of the formula III $$A\text{(H)}_n, \quad \text{(III)}$$

where A and n are as defined in the description, which comprises carrying out the reaction in the presence of a catalyst which contains, as active material, an alkali metal compound of the formula IV (Abstract continued on next page.)

$$M_mAn \quad (IV)$$

in which
M is Li, Na, K, Rb or Cs,
m is the valency of An, and
An is a fluoride, hydroxide, phosphate, formate, acetate or —$OR_5$ radical, and $R_5$ is alkyl having 1 to 4 carbon atoms or phenyl,
and, as support, an alkaline material which, measured in 10% strength by weight aqueous suspension, has a pH>10, selected from one or more groups of substances from the series comprising the alkaline earth metal oxides, hydroxides, aluminates or silicates.

12 Claims, No Drawings

PROCESS FOR THE PREPARATION OF HYDROXYPHENYLPROPIONIC ACID ESTERS

This is a continuation of application Ser. No. 639,466, filed on Jan. 10, 1991, now abandoned.

The present invention relates to a novel process for the preparation of 3-(4-hydroxyphenyl)propionic acid esters.

It is known to prepare compounds of the general formula

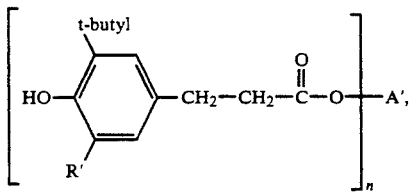

where R' is hydrogen or an alkyl group, n is a number from 2 to 6, and A' is an acyclic or cyclic aliphatic group, by reacting an appropriate hydroxyphenylpropionic acid ester with a compound of the formula A'-(-OH)$_n$, where A' and n are as defined above, in the presence of an element from group 2 of the Periodic Table or in the presence of a compound of one of these elements as catalyst at from 170° to 250° C.

However, the process, a transesterification, is not satisfactory since high reaction temperatures and long reaction times are a prerequisite for achieving the stated conversions and yields, as revealed, for example, in JP-A-62/53942. Further transesterification processes are described in U.S. Pat. Nos. 3,644,482, 4,228,297, 3,644,482 and 3,285,855 and EP-A-102 920.

It has now been found that the course of the reaction can be further improved by choosing a suitable catalyst.

The present invention thus relates to a process for the preparation of a compound of the formula I

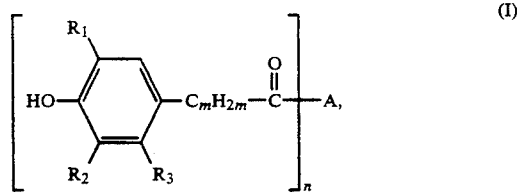

in which $R_1$ and $R_2$ are identical or different and are hydrogen, $C_1$-$C_{18}$alkyl, phenyl, $C_1$-$C_4$alkyl-substituted phenyl, $C_7$-$C_9$phenylalkyl, $C_5$-$C_{12}$cycloalkyl or $C_1$-$C_4$alkyl-substituted $C_5$-$C_{12}$cycloalkyl, $R_3$ is hydrogen or methyl, m is 0, 1, 2 or 3, and n is 1, 2, 3, 4 or 6, where if n=1, A is —OR$_4$ in which $R_4$ is $C_2$-$C_{45}$alkyl, $C_5$-$C_{12}$cycloalkyl, $C_2$-$C_{18}$alkenyl,

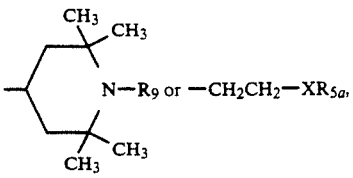

$R_9$ is hydrogen, $C_1$-$C_8$alkyl, $C_3$-$C_5$alkenyl, benzyl,

—O. or —OR$_{9'}$ in which $R_{9'}$ is hydrogen, $C_1$-$C_{25}$alkyl or

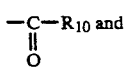

$R_{10}$ is hydrogen or $C_1$-$C_{20}$alkyl,

X is —O—, —S— or

$R_{5a}$ is

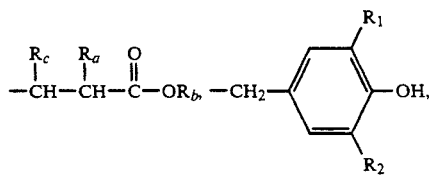

hydrogen, $C_1$-$C_{24}$alkyl, phenyl, $C_5$-$C_{12}$cycloalkyl or

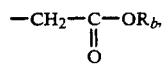

in which $R_a$ is hydrogen or methyl, $R_b$ is hydrogen or $C_1$-$C_{24}$alkyl and $R_c$ is hydrogen or methyl with the proviso that $R_a$ and $R_c$ are not simultaneously methyl, and $R_{6a}$ is $C_1$-$C_{18}$alkyl, phenyl, phenyl which is substituted by one or more alkyl groups having a total of 1 to 24 carbon atoms, or is $C_5$-$C_8$cycloalkyl, or, if n=2, A is —O—$C_xH_{2x}$—O—, —O—(CH$_2$CH$_2$O)$_a$CH$_2$CH$_2$O—, —O—CH$_2$—CH$_2$—B—CH$_2$CH$_2$O—,

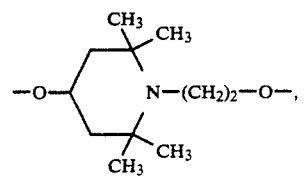

-continued

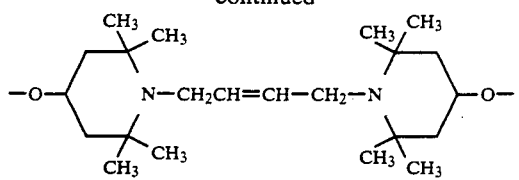

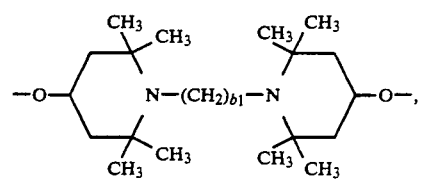

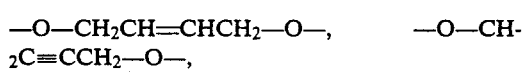

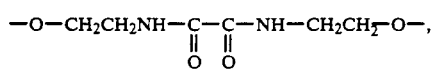

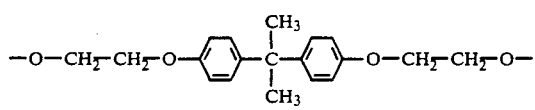

or

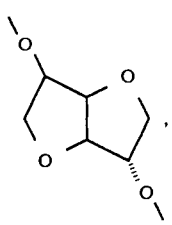

in which
a is a number from 1 to 30 and
x is a number from 2 to 20,
B is —S—,

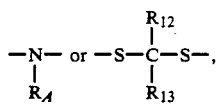

in which
$R_A$ is $C_1-C_{20}$alkyl, phenyl, phenyl which is substituted by one or more alkyl groups having a total of 1 to 20 carbon atoms, or is cyclohexyl or

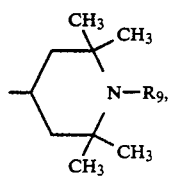

in which $R_9$ is as defined above, and
$R_{12}$ and $R_{13}$, independently of one another, are hydrogen, $C_1-C_{12}$alkyl or phenyl, or $R_{12}$ and $R_{13}$, together with the carbon atom to which they are bonded, form a cycloalkyl ring having 5 to 12 carbon atoms, and
$b_1$ is a number from 2 to 10, or,
if n=3,
A is

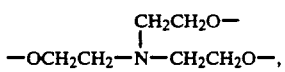

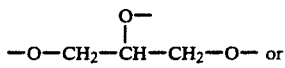

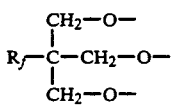

in which
$R_f$ is $C_1-C_{24}$alkyl or phenyl, or,
if n=4,
A is

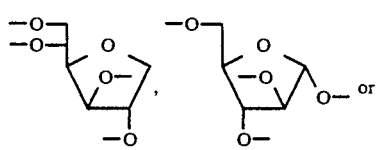

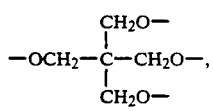

or, if n=6,
A is

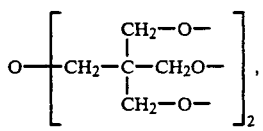

by reacting a compound of the formula II

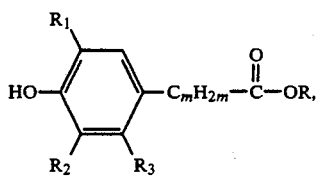   (II)

where m, $R_1$, $R_2$ and $R_3$ are as defined above, and R is alkyl having 1 to 4 carbon atoms, with a compound of the formula III A⟨H⟩$_n$,   (III)

where A and n are as defined above, which comprises carrying out the reaction in the presence of a catalyst which contains, as active material, an alkali metal compound of the formula IV $M_m An$   (IV)

in which

M is Li, Na, K, Rb or Cs, m is the valency of An and

An is a fluoride, hydroxide, phosphate, formate, acetate or —$OR_5$ radical, and $R_5$ is $C_1$-$C_4$alkyl or phenyl, and, as support, an alkaline material which, measured in 10% strength by weight aqueous suspension, has a pH>10, selected from one or more groups of substances from the series comprising the alkaline earth metal oxides, hydroxides, aluminates and silicates.

The present invention also relates to a process for the preparation of a compound which can be used as an intermediate in the process according to the invention, and to a process which covers both preparation of the intermediate and the transesterification thereof to give a compound of the formula (I).

Examples of the substituents in the formulae, I, II and III are given below.

$C_1$-$C_{18}$alkyl $R_1$, $R_2$ and $R_{6a}$ are straight-chain or branched and may be, for example: methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. Alkyl having 1-12 carbon atoms is preferred, and alkyl having 1-8 carbon atoms is particularly preferred.

For $R_1$ and $R_2$, the alkyl groups from the above illustrative list having 1 to 8 carbon atoms should be regarded as expedient and those having 1 to 4 carbon atoms as preferred. $R_1$ and $R_2$ are very particularly preferably the t-butyl group. Furthermore, $R_1$ is preferably —$CH_3$ and $R_2$ is preferably t-butyl, or $R_1$ is preferably isopropyl and $R_2$ is preferably t-butyl. $R_{6a}$ is preferably alkyl having 1-12 carbon atoms. $R_3$ is preferably —H.

R is alkyl having 1 to 4 carbon atoms, such as ethyl, propyl, butyl and in particular methyl.

$R_4$ is, for example, straight-chain or branched alkyl having 1 to 45 carbon atoms. Examples are those given for $R_1$ and $R_2$, as well as eicosyl, heneicosyl, docosyl, triacontyl, etc. $R_4$ is preferably $C_1$-$C_{20}$alkyl and in particular $C_1$-$C_{18}$alkyl.

$R_4$ and $R_{10}$ may be alkyl having 1 to 20 carbon atoms, which means straight-chain or branched alkyl groups, with reference to the abovementioned list of examples for $R_1$ and $R_2$, supplemented by the further example eicosyl. Alkyl groups having 1 to 12 carbon atoms are preferred.

$R_9$ is, for example, alkyl having 1 to 8 carbon atoms, where the alkyl groups may be straight-chain or branched and are methyl, ethyl, propyl, isopropyl, n-butyl, isobutyl, tert-butyl, pentyl, isopentyl, hexyl, heptyl, octyl, 2-ethylhexyl, 2-ethylbutyl, isoamyl, 1-methylpentyl, 1,3-dimethylbutyl, 1,1,3,3-tetramethylbutyl, 1-methylhexyl, isoheptyl or 1-methylheptyl.

An expedient radical for $R_9$ is alkyl having 1 to 4 carbon atoms, accordingly, for example, methyl, ethyl, propyl, isopropyl, n-butyl, isobutyl or tert-butyl.

$R_{9'}$ may be alkyl having 1 to 25 carbon atoms. Examples are analogous to the list for $R_1$ and $R_2$, supplemented by, for example, eicosyl and docosyl. $R_{9'}$ is preferably $C_1$-$C_8$alkyl.

$C_1$-$C_{24}$alkyl $R_b$, $R_f$ and $R_{5a}$ are the straight-chain or branched alkyl groups mentioned, for example, for $R_1$, supplemented, for example, by eicosyl or docosyl. Alkyl groups having 1 to 18 carbon atoms are preferred.

$R_{12}$ and $R_{13}$ are, for example, independently of one another, alkyl having 1 to 12 carbon atoms, where the alkyl groups are straight-chain or branched and, in an illustrative list, may be methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. The appropriate examples having 1 to 8 carbon atoms are preferred.

$R_4$ may preferably be a $C_4$-$C_8$alkyl group. Examples of a group of this type are n-butyl, isobutyl, tert-butyl, pentyl, isopentyl, hexyl, heptyl, octyl, isooctyl, 2-ethylhexyl, 2-ethylbutyl, 1-methylpentyl, 1,3-dimethylbutyl, 1,1,3,3-tetramethylbutyl, 1-methylhexyl, isoheptyl and 1-methylheptyl.

i-$C_8H_{17}$, if mentioned, can also be taken to mean a mixture of isomers.

$C_5$-$C_{12}$cycloalkyl $R_1$, $R_2$, $R_4$ and $R_{5a}$ are, for example, cyclopentyl, cyclohexyl, cycloheptyl, cyclooctyl, cyclodecyl and cyclododecyl. Cyclohexyl is preferred. $C_5$-$C_8$cycloalkyl $R_{6a}$ may be cyclopentyl, cyclohexyl, cycloheptyl or cyclooctyl.

In addition, $R_1$ and $R_2$ are alternatively $C_1$-$C_4$alkyl-substituted cycloalkyl having 5 to 12 carbon atoms. Examples of this are 2- or 4-methylcyclohexyl, dimethylcyclohexyl, trimethylcyclohexyl and t-butylcyclohexyl.

If $R_{6a}$ is phenyl which is substituted by one or more, preferably by one or two, alkyl groups having a total of 1 to 24 carbon atoms, or if $R_4$ is phenyl which is substituted by one or more, preferably by one or two, alkyl groups having a total of 1 to 20 carbon atoms, the examples which can be included amongst the substituents $R_{6a}$ and $R_4$ include methylphenyl, dimethylphenyl, trimethylphenyl, ethylphenyl, diethylphenyl, isopropylphenyl, t-butylphenyl, di-t-butylphenyl, methyl di-t-butylphenyl, tert-octylphenyl and di-tert-octylphenyl.

$C_1$-$C_4$alkyl-substituted phenyl $R_1$ and $R_2$ are, for example, methylphenyl, dimethylphenyl, trimethylphenyl, ethylphenyl, diethylphenyl, isopropylphenyl or 6-butylphenyl.

Finally, $R_{12}$ and $R_{13}$, together with the carbon atom to which they are bonded, may form a cycloalkyl ring having 5 to 12 carbon atoms, for example a cyclopentyl, cyclohexyl, cycloheptyl, cyclooctyl, cyclodecyl or cyclododecyl ring. A cyclohexyl ring is preferred.

$C_7$-$C_9$phenylalkyl $R_1$ and $R_2$ are, for example, benzyl, phenethyl, α-methylbenzyl or α,α-dimethylbenzyl. Benzyl is preferred.

$C_2$-$C_{18}$alkenyl $R_4$ is, for example, vinyl, propenyl, allyl, butenyl, methallyl, hexenyl, decenyl or heptadecenyl.

If m=2, the —$CH_2$—$CH_2$— group, for example, is described, and if m=3, the —$CH_2$—$CH_2$—$CH_2$— or

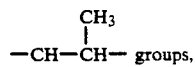

for example, are described.

In preferred compounds of the formula I which can be prepared by the process of the present invention:

$R_1$ is $C_1$-$C_{18}$alkyl, $C_5$-$C_{12}$cycloalkyl, phenyl or benzyl, $R_2$ is hydrogen, $C_1$-$C_{18}$alkyl, $C_5$-$C_{12}$cycloalkyl, phenyl or benzyl, $R_3$ is hydrogen and n is a number from 1 to 4 or 6, and if n=1:

A is —$OR_4$, where $R_4$ is $C_2$-$C_{20}$alkyl, cyclohexyl, $C_2$-$C_{18}$alkenyl or —$CH_2$—$CH_2$—$XR_{5a}$, where X is —O—, —S— or

$R_{5a}$ is hydrogen, $C_1$-$C_{12}$alkyl, phenyl, cyclohexyl or

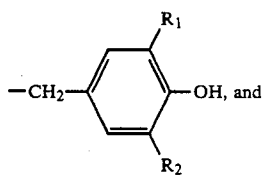

$R_{6a}$ is $C_1$-$C_{12}$alkyl, phenyl, or phenyl which is substituted by one or more alkyl groups having a total of 1 to 18 carbon atoms and, if n=2:

A is —O—$C_xH_{2x}$—O—, —O—$(CH_2CH_2O)_aCH_2CH_2O$—, —O—$CH_2$—$CH_2$—B—$CH_2$—$CH_2O$—,

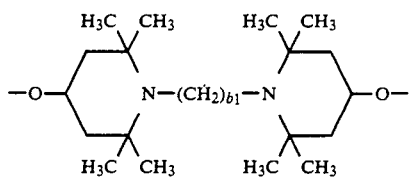

—O—$CH_2CH=CHCH_2$—O—,

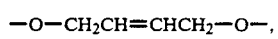

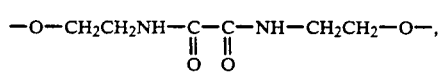

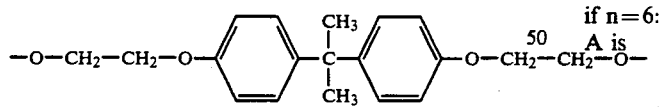

or

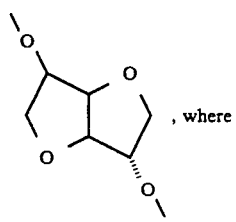, where a is a number from 1 to 12, x is a number from 2 to 12,

B is

—S—oder—N—, where
|
$R_A$ $R_A$ is $C_1$-$C_{12}$alkyl, phenyl, phenyl which is substituted by one or more alkyl groups having a total of 1 to 18 carbon atoms, or is cyclohexyl, and $b_1$ is a number from 2 to 6, if n=3:

A is

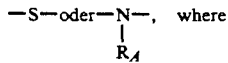

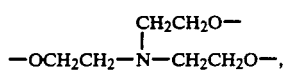

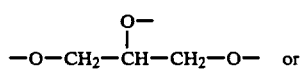

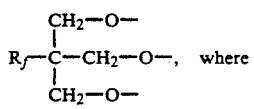

$R_f$ is $C_1$-$C_{12}$alkyl, and, if n=4:

A is

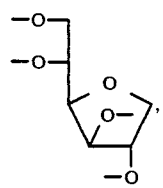

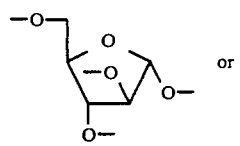

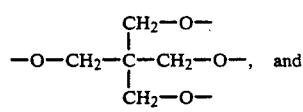, and if n=6:

A is

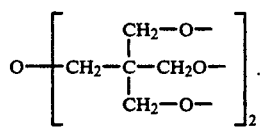

The process of the invention is particularly expedient for the preparation of compounds of the formula I in which:

$R_1$ is $C_1$-$C_{18}$alkyl, cyclohexyl or phenyl, $R_2$ is hydrogen, $C_1$-$C_8$alkyl, cyclohexyl or phenyl, $R_3$ is hydrogen, and n is 1, A is —$OR_4$, where $R_4$ is $C_2$-$C_{18}$alkyl, cyclohexyl, —$CH_2CH=CH_2$, —$(CH_2)_7$—CH=CH—$(CH_2)_7CH_3$,

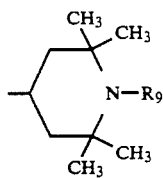

or —CH$_2$CH$_2$XR$_{5a}$, where

R$_9$ is hydrogen, C$_1$–C$_4$alkyl, —O., —O—alkyl having 1 to 4 carbon atoms or cyclohexyl, X is —O—, —S— or

R$_{5a}$ is hydrogen, C$_1$–C$_{18}$alkyl or phenyl, and
R$_{6a}$ is C$_1$–C$_{12}$alkyl or phenyl, and
if n=2:
A is —O—C$_x$H$_{2x}$—O— or —O—(CH$_2$CH$_2$O)$_a$CH$_2$CH$_2$O—, where
x is 2 to 8, and a is 1,2,3 or 4 and
if n=3:
A is —[OCH$_2$CH$_2$]$_3$N, and
if n=4:
A is C—[CH$_2$O]$_4$.

The process of the invention is particularly preferred for the preparation of compounds of the formula I in which:

R$_1$ is tert-butyl,
R$_2$ is hydrogen, methyl or tert-butyl,
R$_3$ is hydrogen, and
if n=1:
A is —OR$_4$, where
R$_4$ is C$_2$–C$_{18}$alkyl, —(CH$_2$)$_7$—CH=CH—(CH$_2$)$_7$CH$_3$,

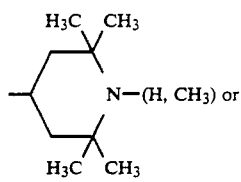

—CH$_2$CH$_2$—SR$_{5a}$, where
R$_{5a}$ is hydrogen or

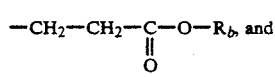

if n=2:
A is —O—C$_x$H$_{2x}$—O—, where
x is 2 to 8,
A is —O—(CH$_2$—CH$_2$—O—)$_a$—CH$_2$—CH$_2$—O—, where
a is 1 to 4,
A is —O—CH$_2$—CH$_2$—B—CH$_2$—CH$_2$—O—, where
B is —S—,

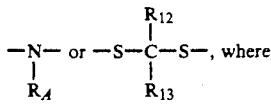

R$_A$ is C$_4$–C$_8$alkyl or phenyl,
A is

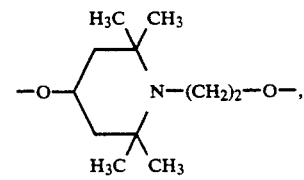

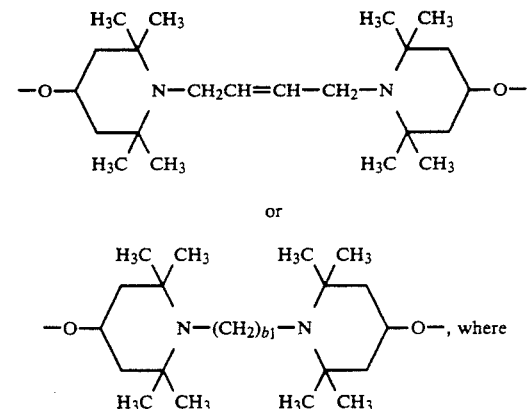

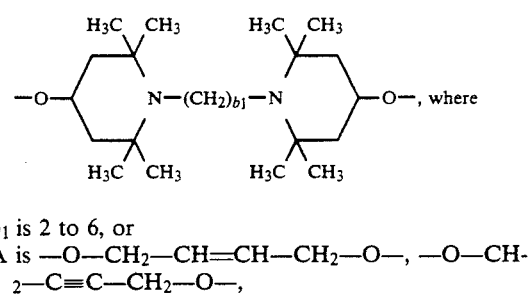

b$_1$ is 2 to 6, or
A is —O—CH$_2$—CH=CH—CH$_2$—O—, —O—CH$_2$—C≡C—CH$_2$—O—,

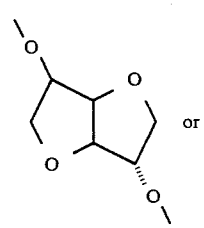

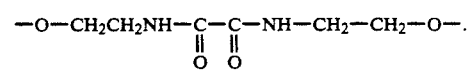

The process of the invention is very particularly preferred for the preparation of compounds of the formula I in which:

R$_1$ is tert-butyl,
R$_2$ is hydrogen, methyl or tert-butyl,
R$_3$ is hydrogen, and
if n=1:
A is —OR$_4$, where
R$_4$ is C$_1$–C$_{18}$alkyl;
or for the preparation of compounds of the formula I, in which:
R$_1$ is tert-butyl,
R$_2$ is hydrogen, methyl or tert-butyl,
R$_3$ is hydrogen, and
if n=2:
A is —O—C$_x$H$_{2x}$—O—, where x is 2 to 6,
A is —O—(CH$_2$—CH$_2$—O)$_a$—CH$_2$—CH$_2$—O—, where
a is 1, 2 or 3, or
A is —O—CH$_2$CH$_2$—B—CH$_2$CH$_2$—O—, where
B is —S— or $$-\underset{\underset{\text{C}_6\text{H}_5}{|}}{\text{N}}-\ ;$$

or for the preparation of compounds of the formula I in which:
R$_1$ is tert-butyl,
R$_2$ is hydrogen, methyl or tert-butyl,
R$_3$ is hydrogen, and
if n=1:
A is —OR$_4$, where
R$_4$ is C$_2$-C$_{18}$alkyl, and
if n=2:
A is —O—C$_x$H$_{2x}$—O— where x=2 bis 6, —OCH$_2$CH$_2$—S—CH$_2$CH$_2$O— or —O(CH$_2$CH$_2$O)$_a$CH$_2$CH$_2$—O—, where
a is 1 to 4.

Particularly preferred processes are those for the preparation of compounds of the formula I in which a is 1 or 2.

Furthermore, preference is given to processes for the preparation of compounds of the formula I in which:
m is 2,
R$_1$ is tert-butyl,
R$_2$ is methyl or tert-butyl,
R$_3$ is hydrogen, and
if n=3:
A is $$-\text{OCH}_2\text{CH}_2-\underset{\underset{\text{CH}_2\text{CH}_2\text{O}-}{|}}{\overset{\overset{\text{CH}_2\text{CH}_2\text{O}-}{|}}{\text{N}}}-\text{CH}_2\text{CH}_2\text{O}-,$$

$$\text{CH}_3-\underset{\underset{\text{CH}_2-\text{O}-}{|}}{\overset{\overset{\text{CH}_2-\text{O}-}{|}}{\text{C}}}-\text{CH}_2-\text{O}-\quad\text{or}$$

$$\text{CH}_3\text{CH}_2-\underset{\underset{\text{CH}_2-\text{O}-}{|}}{\overset{\overset{\text{CH}_2-\text{O}-}{|}}{\text{C}}}-\text{CH}_2-\text{O}-,\ \text{and}$$

if n=4:
A is

[sugar-like ring structure with —O— substituents] or $-\text{O}-\text{CH}_2-\underset{\underset{\text{CH}_2-\text{O}-}{|}}{\overset{\overset{\text{CH}_2-\text{O}-}{|}}{\text{C}}}-\text{CH}_2-\text{O}-$, and if n=6:
A is $$\left[\text{O}-\left[\text{CH}_2-\underset{\underset{\text{CH}_2-\text{O}-}{|}}{\overset{\overset{\text{CH}_2-\text{O}-}{|}}{\text{C}}}-\text{CH}_2\text{O}-\right]\right]_2.$$

Very particular preference is given to the process according to the invention for the preparation of compounds of the type:

$$\left[\text{HO}-\underset{(\text{H}_3\text{C})_3\text{C}}{\overset{\text{C}(\text{CH}_3)_3}{\bigodot}}-\text{CH}_2\text{CH}_2-\underset{\text{O}}{\overset{\|}{\text{C}}}-\text{O}-\text{CH}_2-\text{CH}_2-\right]_2\text{S},$$

$$\left[\text{HO}-\underset{(\text{H}_3\text{C})_3\text{C}}{\overset{\text{C}(\text{CH}_3)_3}{\bigodot}}-\text{CH}_2\text{CH}_2-\underset{\text{O}}{\overset{\|}{\text{C}}}-\text{O}-\text{CH}_2-\right]_4\text{C},$$

$$\left[\text{HO}-\underset{(\text{H}_3\text{C})_3\text{C}}{\overset{\text{C}(\text{CH}_3)_3}{\bigodot}}-\text{CH}_2\text{CH}_2-\underset{\text{O}}{\overset{\|}{\text{C}}}-\text{O}-\text{CH}_2-\text{CH}_2-\right]_2\text{O},$$

$$\text{HO}-\underset{(\text{H}_3\text{C})_3\text{C}}{\overset{\text{C}(\text{CH}_3)_3}{\bigodot}}-\text{CH}_2\text{CH}_2-\underset{\text{O}}{\overset{\|}{\text{C}}}-\text{OR},$$

where R is C$_2$-C$_{18}$alkyl or in particular C$_{18}$H$_{37}$alkyl.

The improvement according to the invention of the process is achieved by using a catalyst which contains, as active material, an alkali metal compound of the formula IV $$\text{M}_m\text{An} \tag{IV}$$

in which
M is Li, Na, K, Rb or Cs,
m is the valency of An, and
An is a fluoride, hydroxide, phosphate, formate, acetate or —OR$_5$ radical and R$_5$ is C$_1$-C$_4$alkyl or phenyl,
and, as support, an alkaline material which, measured in 10% strength by weight aqueous suspension, has a pH>10, selected from one or more groups of substances from the series comprising the alkaline earth metal oxides, hydroxides, aluminates and silicates.

The support substances from the series comprising said alkaline earth metal compounds may be in hydrated or anhydrous form; the hydrated forms are preferred.

Supported catalysts containing an oxide, hydroxide, aluminate or silicate of an alkaline earth metal Mg, Ca, Sr or Ba or a mixture thereof as support are expedient.

Particularly expedient supports are the compounds MgO, Mg(OH)$_2$, CaO, Ca(OH)$_2$, BaO, Ba(OH)$_2$, Ba(OH)$_2$.8H$_2$O, ignited dolomite MgO.CaO, ignited and hydrated dolomite MgCa(OH)$_4$, ignited barytocalcite BaO.CaO, ignited and hydrated barytocalcite BaCa(OH)$_4$, spinel MgAl$_2$O$_4$, MgAl$_2$O$_4$.nH$_2$O, CaAl$_2$O$_4$, CaAl$_2$O$_4$.nH$_2$O, hydrocalumite 2Ca(OH)$_2$.Al(OH)$_3$.nH$_2$O, Ca$_2$SiO$_4$, hillebrandite Ca$_2$SiO$_4$.H$_2$O, foskagite, and mixtures thereof.

Preference is given to CaO, MgO and mixtures of these, for example prepared by roasting dolomite CaCO$_3$.MgCO$_3$, as support.

The support substances are preferably essentially iron-free, i.e. the iron content, including in the form of its compounds, should expediently not exceed 10 ppm. Overall, the support materials should be of high purity, including with respect to other metals, for example copper, lead and other heavy metals. The copper content should expediently be less than 10 ppm, as should the content of heavy metals, for example the lead content should be, for example, less than 10 ppm, and the total (all heavy metals) should, for example, be less than 40 ppm.

Furthermore, the supports are preferably substantially free from carbonate groups. A carbonate content of less than 0.1% by weight should expediently be maintained. Oxygen-transferring anions, for example MnO$_4^-$, CrO$_4^-$, AsO$_4^{3-}$, and NO$_3^-$ should expediently be present to a maximum extent of 100 ppm each, expediently in total to a maximum extent of 200 ppm. Active oxygen should expediently not exceed 100 ppm. Highly acidic anions, for example SO$_4^{2-}$ or Cl$^-$, should expediently be present to a maximum extent of 500 ppm each and to a maximum extent of 1000 ppm in total.

Expedient supported catalysts contain, as active material, the hydroxides or fluorides of the alkali metals Na, K, Rb or Cs.

Preferred active materials are KOH, KF, NaOH, NaF and CsF, particularly preferably KOH and KF.

The proportion of the active material is, for example, from 0.15 to 30% by weight, computed based on the anhydrous support. The percentages are computed on the basis of the corresponding alkali metal alone, i.e. without taking into account the respective anion, while the data for the support is based on these in total.

From 0.15 to 10% of active material are expediently present, and, in a preferred embodiment, from 1 to 10% by weight of active material are present, in each case based on the alkali metal and the anhydrous support.

Very particularly suitable catalysts for the reaction of compounds of the formula II with compounds of the formula III to give the corresponding compounds of the formula I are those which contain ignited and hydrated CaO or CaO and MgO, the latter mixture being obtainable, for example, by ignition and subsequent hydration of dolomite (CaCO$_3$.MgCO$_3$), and from 5 to 15% by weight, preferably 10% by weight of K as KF or KOH.

Particularly preferred catalysts are KF as the active material on Ca(OH)$_2$ as support, KOH on Ca(OH)$_2$ and KF on ignited and hydrated dolomite.

The catalysts described above are particularly suitable in a process for the preparation of a compound of the general formula Ia

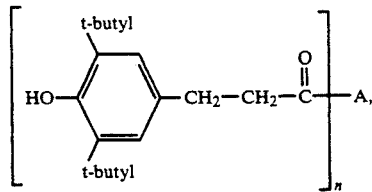

where A and n are as defined above, by reacting a compound of the formula IIa

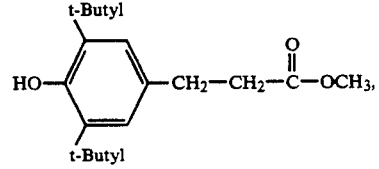

with a compound A$-$(H)$_n$ of the formula III, as described above.

The present invention also relates to the use of catalysts as described above in a process for reacting a compound of the formula II with a compound of the formula III to give a compound of the formula I and preferably for reacting a compound of the formula IIa with a compound of the formula III to give a compound of the formula Ia. The meanings of the compounds of the formulae I, II, IIa and III are given above.

Catalysts of the invention containing Ca-, Mg- or Ba-containing supports are obtainable, for example, by calcining compounds which can be converted into their oxides by thermal treatment, such as Ca(OH)$_2$, CaCO$_3$, Mg(OH)$_2$, MgCO$_3$, hydromagnesite MgCO$_3$.Mg(OH)$_2$.nH$_2$O, dolomite MgCO$_3$.CaCO$_3$ or Ba(OH)$_2$.8H$_2$O, at a temperature of from 600° to 1100° C., preferably from 900° to 1100° C.

The supports produced should contain a maximum of 0.1% by weight of CO$_3^{2-}$. In order to prevent carbonisation, the supports should expediently be protected against ambient air during further treatment and storage by an inert gas or by vacuum.

A support prepared in this way can expediently be quenched using carbonate-free water, forming the corresponding hydroxide, which can itself be further treated with aqueous solution of at least one salt of Li, Na, K, Rb or Cs. It is also possible to quench the support directly using an aqueous solution of a salt of Li, Na, K, Rb or Cs, forming alongside one another, corresponding to the supply of water and alkaline metal salts, the corresponding hydroxides and further salts of alkaline earth metals and alkali metals. During the quenching process, the temperature of the reaction mixture should expediently not exceed 90° C. The temperature can be partially controlled by means of the amount of water added.

In general, the catalyst after quenching should be in the form of a pasty material in which the amount of water should expediently not exceed the weight of the support by 4–5 times. Drying is preferably carried out in an inert atmosphere, for example under N$_2$, or in vacuo. Drying temperatures may be between 80° and 400° C., expediently 350° C., and it has proven expedient to carry out the drying under an inert gas in a first step for from 3 to 5 hours at 90° C. and in a second step for from 5 to 24 hours at a temperature rising to 350° C. or for from 3 to 5 hours at 150°-200° C., expediently at 160° C. in vacuo.

After this, catalysts prepared in this way generally have a high-strength structure similar to that of ceramics and can be adjusted to the desired weight, for example by breaking and if necessary grinding.

If the catalyst is employed as a suspension, it is advantageous, in order to ensure good filterability later, to reduce the grain size to from 0.2 to 0.5 mm. If the aim is a reaction in a fixed bed, a grain size of, for example, around 5 mm is appropriate.

The catalysts may also be obtained by physically mixing the support with an active material.

The mixing can be carried out in a manner known per se, and, in accordance with the desired strength or grain size of the finished catalyst, the mixing can also be carried out for example in a ball mill. The mixing operation is expediently carried out in the absence of air, accordingly either under an inert gas, such as nitrogen or a noble gas, or in vacuo. In this case, the constituents are generally mixed in the dry state expediently in hydrated form, for example KOH with $Ca(OH)_2$.

The catalyst may be in disperse form in the reactants and is filtered off when the reaction is complete. The catalyst exhausted by use can be regenerated and reused or discarded. It is also possible to arrange the catalyst in a fixed bed and to carry out the reaction, for example, in a flow reactor (continuous procedure).

The process is expediently carried out by reacting the starting materials either dissolved in a solvent or, if they are not liquid, converted into a melt by increasing the temperature.

The solvents used are customary compounds and mixtures, for example aromatic hydrocarbons, such as benzene, and alkyl-substituted or halogen-substituted benzenes, in particular toluene, xylene or dichlorobenzene, high-boiling aliphatic hydrocarbons, such as high-boiling paraffins, or aprotic solvents, such as dimethylformamide or dimethylanilin.

The catalyst is added to the reaction mixture, for example, in amounts of from 0.1 to 10 mol-%, expediently of from 1 to 5 mol-%, preferably from 2 to 4 mol-%, of active material, based on the compounds of the formula III.

The ratio between the compounds of the formula II or IIa and the compounds of the formula III in the reaction mixture is not crucial and may be, for example, from 0.8 to 1.3 mol of compound II or IIa per equivalent of the compound III. From 0.95 to 1.2 mol of the compound II or IIa per equivalent of the compound III, preferably from 1.0 to 1.05 mol of the compound II or IIa per equivalent of the compound III, are expedient.

The reaction temperature may be, for example, between 110° and 250° C., expediently between 130° and 195° C., preferably between 130° and 170° C.

The reaction of a compound of the formula II or IIa with a compound of the formula III generally takes between 1 and 5 hours, expediently between 1 and 4 hours, preferably between 1 and 3 hours, before optimum yields are achieved.

The catalyst may, for example, be suspended in the reaction mixture in powder form or broken into pieces. The process can also be carried out using the catalyst in a fixed bed.

When the reaction is complete, the catalyst, if in suspension, can be separated off, for example filtered off, and the end product can be isolated by measures which are known per se, such as crystallisation from a solvent, such as methanol, isopropanol, a methanol/water mixture, etc.

If necessary, the reaction mixture and/or the end product can be neutralised using an acid, for example formic acid, acetic acid, sulfuric acid, hydrochloric acid, etc.

The compounds of the formula II and III employed in the process according to the invention are known or can be obtained by processes which are known per se. Such starting compounds are described in the documents cited in the introduction.

The compounds of the formulae I and Ia prepared according to the invention are, for example, valuable antioxidants against oxidative, thermal or actinic degradation of sensitive organic materials. Such materials are, for example, synthetic polymers or functional fluids, such as lubricants, hydraulic fluids or metalworking fluids, etc.

The present invention also relates to a novel process for the preparation of 3-(4-hydroxyphenyl)propionic acid esters of the formula V

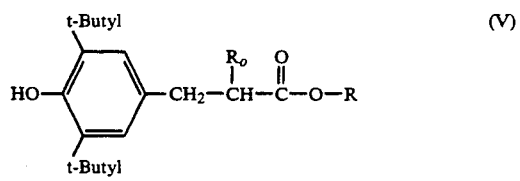

in which $R_o$ and R are as defined below.

It is known to prepare compounds of this type, for example, from a hydroxyphenyl and an acrylate in the presence of a catalyst. According to U.S. Pat. No. 4,659,863, this reaction is carried out in the presence of an alkali metal catalyst and a solubiliser for the catalyst.

U.S. Pat. No. 3,840,585 discloses a process of this type which is carried out in the presence of a catalytic amount of hydrides, for example $NaBH_4$, $LiBH_4$ or $Mg(AlH_4)_2$.

U.S. Pat. No. 3,364,250 discloses, for example, a process in which a catalyst is prepared from potassium metal and tert-butyl alcohol; the above reaction then proceeds in the presence of this catalyst.

U.S. Pat. No. 3,247,240 describes a process of the abovementioned type which involves the reaction of a dialkylhydroxyphenol with an acrylate in the presence of a basic catalyst, for example from the series comprising alkali metal alkoxides, alkali metal hydroxides and furthermore alkaline earth metal alkoxides.

DE-A-23 64 126 discloses a process for the preparation of hydroxyalkylphenyl derivatives by reacting appropriate phenols with methyl acrylate in the presence of a catalyst, for example an alkali metal hydride or alkali metal hydroxide. The reaction mixture can then be transesterified, for example using a long-chain alcohol and using a second catalyst.

DE-A-23 64 121 discloses a further process in which, for example, 2,6-di-tert-butylphenol, n-octadecylalcohol and methyl methacrylate can be reacted directly in the presence of sodium methoxide to give n-octadecyl β-(3,5-di-tert-butyl-4-hydroxyphenyl)propionate.

It has now been found that the reaction procedure can be further improved by using certain catalysts. In the process of the invention, a compound of the general formula V

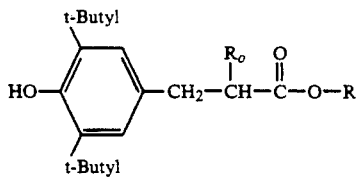

in which
R$_o$ is hydrogen or C$_1$-C$_4$alkyl, in particular hydrogen or methyl, and
R is C$_1$-C$_4$alkyl,
is prepared by reacting 2,6-di-tert-butylphenol with an acrylate of the formula VI

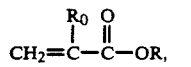

in which R$_0$ and R are as defined above, which comprises carrying out the reaction in the presence of a catalyst which contains, as active material, a component of the formula IV M$_m$An  (IV)

in which
M is Na, K, Rb or Cs,
m is the valency of An and
An is a fluoride, hydroxide or —OR$_5$ radical, and R$_5$ is C$_1$-C$_4$alkyl or phenyl,
and, as support, an alkaline material which, measured in 10% strength by weight aqueous suspension, has a pH > 10, selected from one or more groups of substances from the series comprising the hydrated alkaline earth metal oxides, aluminates and silicates.

If, in the active material, An is an —OR$_5$ radical and if R$_5$ is alkyl having 1 to 4 carbon atoms, examples of this are methyl, ethyl, n-propyl, i-propyl, n-butyl, sec-butyl and tert-butyl.

Examples of preferred supports are Mg(OH)$_2$, Ca(OH)$_2$, Sr(OH)$_2$, Ba(OH)$_2$, MgAl$_2$O$_4$.nH$_2$O, CaAl$_2$O$_4$.nH$_2$O, hydrocalumite 2Ca(OH)$_2$.Al(OH)$_3$.nH$_2$O, hillebrandite Ca$_2$SiO$_4$.H$_2$O, ignited and hydrated dolomite MgCa(OH)$_4$, ignited and hydrated barytocalcite CaBa(OH)$_4$ and mixtures of said substances with one another.

In this process too, the support substances are preferably essentially iron-free, i.e. the iron content, including in the form of its compounds, should expediently not exceed 10 ppm. Overall, the support materials should be of high purity, including with respect to other metals, for example copper, lead and other heavy metals. The copper content should expediently be less than 10 ppm, as should the content of heavy metals, for example the lead content should be, for example, less than 10 ppm, and the total (all heavy metals) should, for example, be less than 20 ppm.

Furthermore, the supports are preferably substantially free from carbonate groups and in particular from carbonate ions. A carbonate content of less than 0.1% by weight should expediently be maintained. Oxygen-transferring anions, for example AsO$_4{}^{3-}$, NO$_3{}^-$, CrO$_4{}^-$, MnO$_4{}^-$ should expediently be present to a maximum extent of 100 ppm each, expediently in total to a maximum extent of 200 ppm. Active oxygen should expediently not exceed a limit of 100 ppm. Strong anions, such as acidic anions, for example SO$_4{}^{2-}$ or Cl$^-$, should expediently be present to a maximum extent of 500 ppm each and to a maximum extent of 1000 ppm in total.

M is preferably Na or K.

Preferred active materials are KOH, KF, NaOH, CsF and NaF, particularly preferably KOH and KF.

The proportion of the active material is, for example, from 0.15 to 30% by weight, computed based on the anhydrous support. The percentages are computed on the basis of the corresponding alkali metal ion alone, i.e. without taking into account the respective anion, while the data for the anhydrous support is based on these in total.

From 0.15 to 10% of active material are expediently present, and, in a preferred embodiment, from 1 to 10% by weight of active material are present, in each case based on the alkali metal ion and the anhydrous support.

Very particularly suitable catalysts for the reaction of compounds of the formula VI with 2,6-di-tert-butylphenol to give the corresponding compounds of the formula I are those which contain ignited and hydrated CaO or CaO and MgO, the latter mixture being obtainable, for example, by ignition and subsequent hydration of dolomite (CaCO$_3$.MgCO$_3$), and from 5 to 15% by weight, preferably 10% by weight, of KF or KOH.

Particularly preferred catalysts are KF as the active material on Ca(OH)$_2$ as support, KOH on Ca(OH)$_2$ and KF on ignited and hydrated dolomite.

The above-described catalysts which can be employed according to the invention are particularly suitable in a process for the preparation of a compound of the general formula V in which R$_o$ is —H or —CH$_3$ and R is as defined above, and very particularly for the preparation of

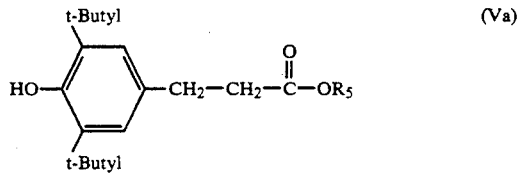

or

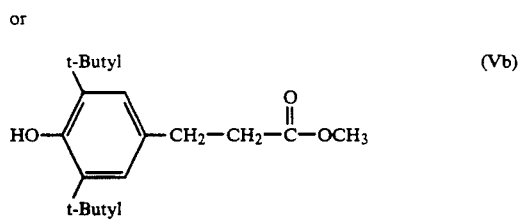

by reacting a compound of the formula VIa

or

with 2,6-di-tert-butylphenol, as described above.

The present invention also relates to the use of catalysts as described above in a process for reacting a compound of the formula VI with 2,6-di-tert-butylphenol to give a compound of the formula V, expediently for the reaction of a compound of the formula VIa with 2,6-di-tert-butylphenol to give a compound of the formula Ia and preferably for the reaction of a compound of the formula VIb with 2,6-di-tert-butylphenol to give a compound of the formula Vb. The meanings of the compounds of the formulae V, Va, Vb, VI, VIa and VIb are given above.

Catalysts of the invention containing Ca-, Mg- or Ba-containing supports are obtainable, for example, by calcining Cao, MgO or BaO or compounds which can be converted into their oxides by thermal treatment, such as $Ca(OH)_2$, $CaCO_3$, $Mg(OH)_2$, $MgCO_3$ or $Mg(OH)_2$ at a temperature of from 600° to 1100° C., preferably from 900° to 1100° C. or by calcining dolomite or barytocalcite at elevated temperature.

The supports produced should expediently contain 0.1% by weight of $CO_3^{2-}$. In order to prevent carbonisation, the supports should expediently be protected against ambient air during further treatment and storage by an inert gas or by vacuum.

A support prepared in this way can expediently be quenched using carbonate-free water, forming the corresponding hydroxide, which can itself be further treated with an aqueous solution of at least one salt of Na, K, Rb or Cs. It is also possible to quench the support directly using an aqueous solution of a salt of Na, K, Rb or Cs, forming alongside one another, corresponding to the supply of water and alkaline metal salts, the corresponding hydroxides and further salts of alkaline earth metals and alkali metals. During the quenching process, the temperature of the reaction mixture should expediently not exceed 90° C. The temperature can be partially controlled by means of the amount of water added.

In general, the catalyst after quenching is advantageously in the form of a pasty material. To this end, the amount of water can make up up to 4-5 times the amount of the anhydrous support. The pasty material is preferably dried in an inert atmosphere, for example under $N_2$, or in vacuo. Drying temperatures may be between 80° and 400° C., expediently 350° C., and it has proven expedient to carry out the drying under an inert gas in a first step for from 3 to 5 hours at 90° C. and in a second step for from 5 to 24 hours at a temperature rising to 350° C. or for from 3 to 5 hours at 150°-200° C., expediently at 160° C. in vacuo.

After this, catalysts prepared in this way generally have a high-strength structure similar to that of ceramics and can be adjusted to the desired weight, for example by breaking and if necessary grinding.

If the catalyst is employed as a suspension, it is advantageous, in order to ensure good filterability later, to reduce the grain size to from 0.2 to 0.5 mm. If the aim is a reaction in a fixed bed, a grain size of, for example, around 5 mm is appropriate.

The catalysts according to the invention may also be obtained by physically mixing the support with an active material.

The mixing can be carried out in a manner known per se, and, in accordance with the desired strength or grain size of the finished catalyst, the mixing can also be carried out for example in a ball mill. The mixing operation is expediently carried out in the absence of air, accordingly either under an inert gas, such as nitrogen or a noble gas, or in vacuo. In this case, the constituents are generally mixed in the dry, hydrolysed state.

The catalyst may be in disperse form in the reactants and is filtered off when the reaction is complete. The addition of a solvent, for example toluene, may accelerate the filtration process. The catalyst exhausted by use can be regenerated and re-used or discarded. The regeneration may also be effected by washing with a solvent, for example toluene, drying and freeing from solvent and re-impregnating with alkali metal salts and subsequently drying. It is also possible to arrange the catalyst in a fixed bed and to carry out the reaction, for example, in a flow reactor (continuous procedure).

The process is expediently carried out by reacting the starting materials either dissolved in a solvent or, if they are not liquid, converted into a melt by increasing the temperature.

The solvents used are customary compounds and mixtures, for example aromatic hydrocarbons, such as benzene, and alkyl-substituted or halogen-substituted benzenes, in particular toluene, xylene or dichlorobenzene, high-boiling aliphatic hydrocarbons, such as high-boiling paraffins, or aprotic solvents, such as dimethylformamide or dimethylaniline, dimethyl sulfoxide or alcohols, such as tert-butanol.

The catalyst is added to the reaction mixture, for example, in amounts of from 0.1 to 10 mol-%, expediently from 0.5 to 5 mol-%, particularly expediently from 1 to 5 mol-% and preferably from 2 to 4 mol-%, of active material, based on 2,6-di-tert-butylphenol.

The ratio between the compounds of the formula VI and 2,6-di-tert-butylphenol in the reaction mixture is not crucial and may be, for example, from 0.8 to 1.5 mol of compound VI per mole of 2,6-di-tert-butylphenol. From 0.95 to 1.2 mol of the compound VI per mole of 2,6-di-tert-butylphenol preferably from 1.0 to 1.05 mol of the compound VI per mole of 2,6-di-tert-butylphenol are expedient.

The reaction temperature may be, for example, between 85° and 190° C., and expediently between 100° and 145° C.

The reaction of a compound of the formula VI with 2,6-di-tert-butylphenol generally takes between 1 and 5 hours, expediently between 1 and 4 hours, preferably between 1 and 3 hours, before optimum yields are achieved.

The catalyst may, for example, be suspended in the reaction mixture in powder form or broken into pieces. The process can also be carried out using the catalyst in a fixed bed.

When the reaction is complete, the catalyst, if in suspension, can be separated off, for example filtered off, and the end product can be isolated by measures which are known per se, such as crystallisation from a solvent, such as methanol, isopropanol, a methanol/water mixture, etc.

If necessary, the reaction mixture and/or the end product can be neutralised using an acid, for example formic acid, acetic acid, sulfuric acid, hydrochloric acid, etc.

The compounds of the formula V prepared according to the invention are, for example, valuable intermediates which can also be used according to the invention in a process for the preparation of a compound of the general formula VII

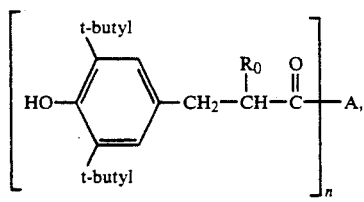 (VII)

in which
R₀ is hydrogen or $C_1$-$C_4$alkyl, in particular hydrogen or methyl, and
n is 1,2,3,4 or 6, and
if n=1,
A is —OR₄ in which
R₄ is $C_2$-$C_{45}$alkyl, $C_5$-$C_{12}$cycloalkyl, $C_2$-$C_{18}$alkenyl,

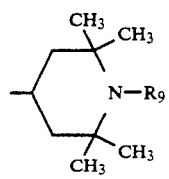

or —CH₂CH₂—XR₅ₐ, in which
R₉ is hydrogen, $C_1$-$C_8$alkyl,

—O. or —OR₉·, in which
R₉· is hydrogen or $C_1$-$C_{25}$alkyl or

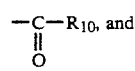

R₁₀ is hydrogen or alkyl having 1 to 20 carbon atoms,
X is —O—, —S— or

R₅ₐ is

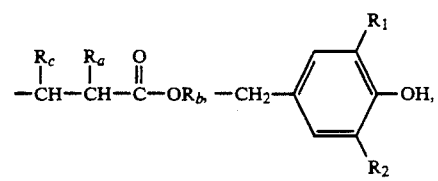

hydrogen, $C_1$-$C_{24}$alkyl, phenyl, $C_5$-$C_{12}$cycloalkyl or

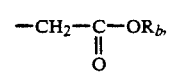

in which
Rₐ is hydrogen or methyl,
R_b is hydrogen or $C_1$-$C_{24}$alkyl and

R_c is hydrogen or methyl, with the proviso that Rₐ and R_c are not simultaneously methyl, and
R₆ₐ is $C_1$-$C_{18}$alkyl, phenyl, phenyl which is substituted by one or more alkyl groups having a total of 1 to 24 carbon atoms, or is $C_5$-$C_8$cycloalkyl, or,
if n=2,
A is —O—$C_xH_{2x}$—O—, —O—(CH₂CH₂O)ₐCH₂CH₂O—, —O—CH₂—CH₂—B—CH₂CH₂O—,

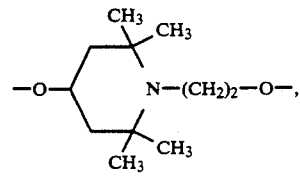

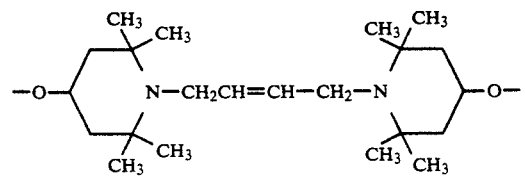

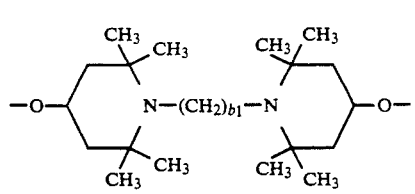

—O—CH₂CH=CHCH₂—O—, —O—CH₂C≡CCH₂—O—,

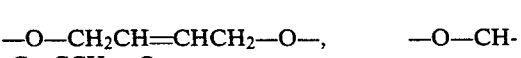

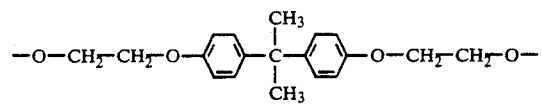

or

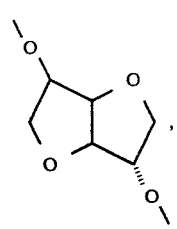

in which
a is a number from 1 to 30
x is a number from 2 to 20,
B is —S—,

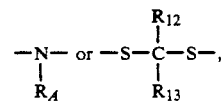

in which
R_A is $C_1$-$C_{20}$alkyl having 1 to 20 carbon atoms, phenyl, phenyl which is substituted by one or more alkyl groups having a total of 1 to 20 carbon atoms, or is cyclohexyl or

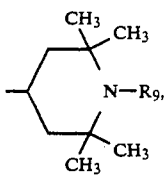

where $R_9$ is as defined above, and $R_{12}$ and $R_{13}$, independently of one another, are hydrogen, $C_1$-$C_{12}$alkyl or phenyl, or $R_{12}$ and $R_{13}$, together with the carbon atom to which they are bonded, form a cycloalkyl ring having 5 to 12 carbon atoms, and $b_1$ is a number from 2 to 10, or,
if $n=3$,
A is

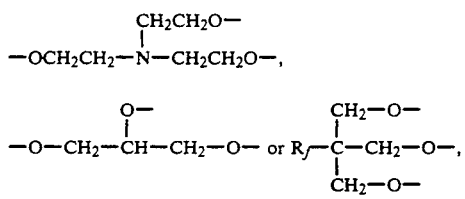

in which
$R_f$ is $C_1$-$C_{24}$alkyl or phenyl, or,
if $n=4$,
A is

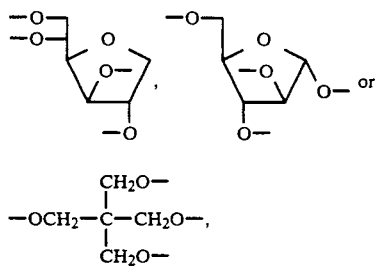

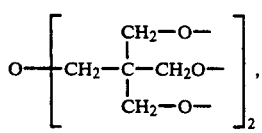

if $n=6$,
A is

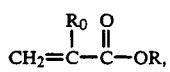

which comprises reacting a compound of the formula VI

in which $R_0$ is hydrogen or $C_1$-$C_4$alkyl and R is $C_1$-$C_4$alkyl, with 2,6-di-tert-butylphenol in a first step to give a compound of the formula V, and reacting the latter, without isolation from the reaction mixture, in a second step with a compound of the formula III

where A and n are as defined above, both steps being carried out in the presence of a catalyst which contains, as active material, a component of the formula IV $$M_mAn \qquad (IV)$$

in which

M is Na, K, Rb or Cs, m is the valency of An and

An is a fluoride, hydroxide or —$OR_5$ radical, and $R_5$ is $C_1$-$C_4$alkyl or phenyl, and, as support, an alkaline material which, measured in 10% strength by weight suspension, has a pH>10, selected from one or more groups of substances from the series comprising the hydrated alkaline earth metal oxides, aluminates and silicates.

The substituent A in the formula VII is as defined above, for example the individual radicals mentioned below.

In $C_1$-$C_{18}$alkyl $R_{6a}$, the alkyl group may be straight-chain or branched and may be, for example: methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. Alkyl having 1-12 carbon atoms is preferred, and alkyl having 1-8 carbon atoms is particularly preferred.

$R_4$ is, for example, straight-chain or branched alkyl having 2 to 45 carbon atoms. Examples are those indicated for $R_{6a}$, supplemented by eicosyl, hemicosyl, docosyl, triacontyl, etc. $R_4$ is preferably $C_5$-$C_{20}$alkyl and in particular $C_8$-$C_{18}$alkyl.

If $R_4$ is alkyl having 2, 3 or 4 carbon atoms, the transesterification of the compound of the formula I proceeds from a compound in which $R_5$ is methyl, methyl or ethyl, or methyl, ethyl or propyl respectively.

$R_A$ and $R_{10}$ may be alkyl having 1 to 20 carbon atoms, meaning straight-chain or branched alkyl groups, the abovementioned list of examples for $R_{6a}$ being supplemented by the further example eicosyl. Alkyl groups having 1 to 12 carbon atoms are preferred.

$R_9$ is, for example, alkyl having 1 to 8 carbon atoms, where the alkyl groups may be straight-chain or branched and are methyl, ethyl, propyl, isopropyl, n-butyl, isobutyl, tert-butyl, pentyl, isopentyl, hexyl, heptyl, octyl, 2-ethylhexyl, 2-ethylbutyl, isoamyl, 1-methylpentyl, 1,3-dimethylbutyl, 1,1,3,3-tetramethylbutyl, 1-methylhexyl, isoheptyl or 1-methylheptyl.

An expedient radical for $R_9$ is alkyl having 1 to 4 carbon atoms, accordingly, for example, methyl, ethyl, propyl, isopropyl, n-butyl, isobutyl or tert-butyl.

$R_{9'}$ may be alkyl having 1 to 25 carbon atoms. Examples are given correspondingly in the list for $R_{6a}$, supplemented by, for example, eicosyl and docosyl. $R_{9'}$ is preferably $C_1$-$C_8$alkyl.

If $R_b$, $R_f$ or $R_{5a}$ is an alkyl group having 1 to 24 carbon atoms, these include the straight-chain or branched alkyl groups mentioned as examples for $R_{6a}$, supplemented, for example, by eicosyl and docosyl. Alkyl groups having 1 to 18 carbon atoms are preferred.

$R_{12}$ and $R_{13}$ are, for example, independently of one another, alkyl having 1 to 12 carbon atoms, where the alkyl groups may be straight-chain or branched and are, in an illustrative list, methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. The corresponding examples having 1 to 8 carbon atoms are preferred.

In preferred form, $R_A$ may be a $C_4$-$C_8$alkyl group, and examples of groups of this type are n-butyl, isobutyl, tert-butyl, pentyl, isopentyl, hexyl, heptyl, octyl, isooctyl, 2-ethylhexyl, 2-ethylbutyl, 1-methylpentyl, 1,3-dimethylbutyl, 1,1,3,3-tetramethylbutyl, 1-methylhexyl, isoheptyl or 1-methylheptyl.

If mentioned, i-$C_8H_{17}$ may be taken to mean a mixture of isomers.

$C_5$-$C_{12}$Cycloalkyl $R_6$ or $R_{5a}$ includes, for example, cyclopentyl, cyclohexyl, cycloheptyl, cyclooctyl, cyclodecyl and cyclododecyl. Cyclohexyl is preferred.

$C_5$-$C_8$Cycloalkyl $R_{6a}$ may be cyclopentyl, cyclohexyl, cycloheptyl or cyclooctyl.

If $R_{6a}$ is phenyl which is substituted by one or more, preferably by one or two, alkyl groups having a total of 1 to 24 carbon atoms, or if $R_A$ is phenyl which is substituted by one or more, preferably by one or two, alkyl groups having a total of 1 to 20 carbon atoms, the examples which can be assigned to the substituents $R_{6a}$ and $R_A$ include methylphenyl, dimethylphenyl, trimethylphenyl, ethylphenyl, diethylphenyl, isopropylphenyl, t-butylphenyl, di-t-butylphenyl, methyl-di-t-butylphenyl, tert-octylphenyl and di-tert-octylphenyl.

Finally, $R_{12}$ and $R_{13}$, together with the carbon atom to which they are bonded, may form a cycloalkyl ring having 5 to 12 carbon atoms, for example a cyclopentyl, cyclohexyl, cycloheptyl, cyclooctyl, cyclodecyl or cyclododecyl ring. A cyclohexyl ring is preferred.

Examples of $C_2$-$C_{18}$alkenyl $R_4$ are vinyl, propenyl, allyl, butenyl, methallyl, hexenyl, decenyl or heptadecenyl.

If m=2, the group, for example —$CH_2$—$CH_2$— described, and if m=3, the groups, for example —$CH_2$—$CH_2$—$CH_2$— or

are described.

In expedient compounds of the formula VII which can be prepared by the process of the present invention, n is a number from 1 to 4 or 6, and
if n=1:
A is —$OR_4$ where
$R_4$ is $C_2$-$C_{20}$alkyl, cyclohexyl, $C_2$-$C_{18}$alkenyl or —$CH_2$—$CH_2$—$XR_{5a}$ where
X is —O—, —S— or

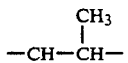

$R_{5a}$ is hydrogen, $C_1$-$C_{12}$alkyl, phenyl, cyclohexyl or

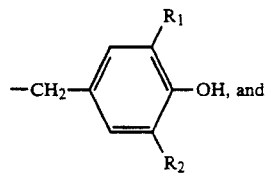

$R_{6a}$ is $C_1$-$C_{12}$alkyl, phenyl or phenyl which is substituted by one or more alkyl groups having a total of 1 to 18 carbon atoms, and
if n=2:
A is —O—$C_xH_{2x}$—O—, —O—($CH_2CH_2O)_aCH_2CH_2O$—, —O—$CH_2$—$CH_2$—B—$CH_2$—$CH_2O$—,

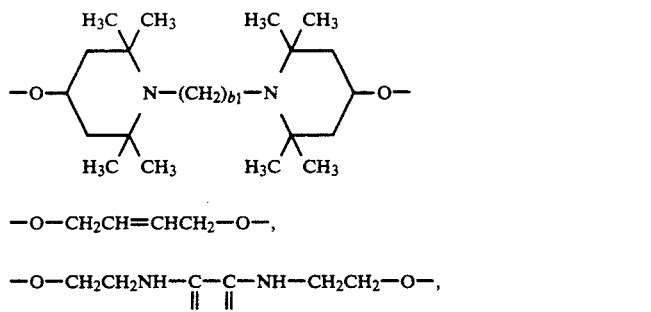

—O—$CH_2CH=CHCH_2$—O—,

—O—$CH_2CH_2NH$—C—C—$NH$—$CH_2CH_2$—O—,
         ‖  ‖
         O  O

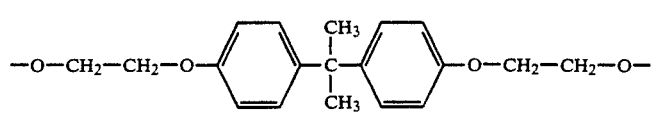

or

-continued

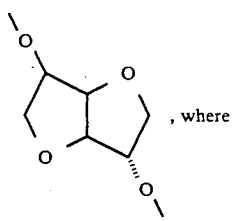, where a is a number from 1 to 12,
x is a number from 2 to 12,
B is —S— or

$R_A$ is $C_1$-$C_{12}$alkyl, phenyl or phenyl which is substituted by one or more alkyl groups having a total of 1 to 18 carbon atoms, or is cyclohexyl, and
$b_1$ is a number from 2 to 6, and
if n=3:
A is

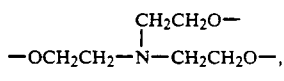

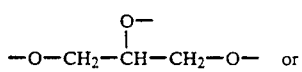  or

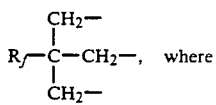, where $R_f$ is $C_1$-$C_{12}$alkyl, and
if n=4:
A is

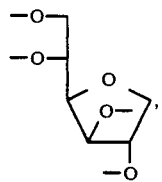,

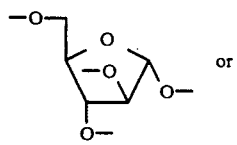 or

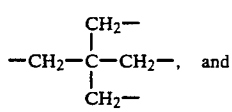, and if n=6:
A is $$O \begin{bmatrix} & CH_2-O- & \\ -CH_2-C-CH_2O- & \\ & CH_2-O- & \end{bmatrix}_2 .$$

The process of the invention is particularly expedient for the preparation of a compound of the formula VII in which:
if n is 1,
A is —$OR_4$, where
$R_4$ is $C_2$-$C_{18}$alkyl, cyclohexyl, —$CH_2CH=CH_2$, —$(CH_2)_7$—CH=CH—$(CH_2)_7CH_3$,

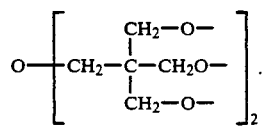

or —$CH_2CH_2XR_{5a}$,
$R_9$ is hydrogen, $C_1$-$C_4$alkyl, —O., —O—alkyl having 1 to 4 carbon atoms or cyclohexyl,
X is —O—, —S— or

, $R_{5a}$ is hydrogen, $C_1$-$C_{18}$alkyl or phenyl, and
$R_{6a}$ is $C_1$-$C_{12}$alkyl or phenyl, and
if n=2:
A is —O—$C_xH_{2x}$—O— or —O—$(CH_2C$-$H_2O)_a CH_2CH_2O$—, where
x is 2 to 8 and a is 1, 2, 3 or 4 and
if n=3:
A is —$OCH_2CH_2]_3N$ and
if n=4:
A is C—$CH_2O]_4$.
The process of the invention is preferred for the preparation of a compound of the formula VII in which:
if n=1,
A is —$OR_4$, where
$R_4$ is $C_2$-$C_{18}$alkyl,

—$(CH_2)_7$—CH=CH—$(CH_2)_7CH_3$,

-continued

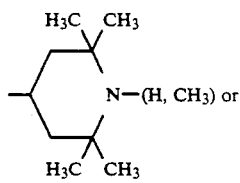

—CH$_2$CH$_2$—SR$_{5a}$, where

R$_{5a}$ is hydrogen or

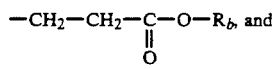

if n=2:

A is —O—C$_x$H$_{2x}$—O—, where
x is 2 to 8,
A is —O—(CH$_2$—CH$_2$—O—)$_a$—CH$_2$—CH$_2$—O—, where
a is 1 to 4,
A is —O—CH$_2$—CH$_2$—B—CH$_2$—CH$_2$—O— where
B is —S—,

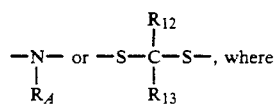

R$_A$ is C$_4$-C$_8$alkyl or phenyl,
A is

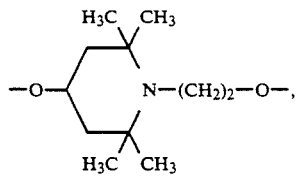

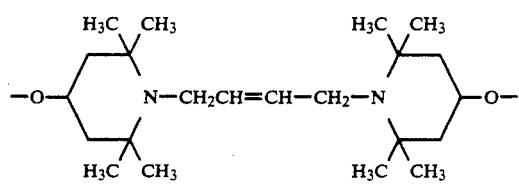

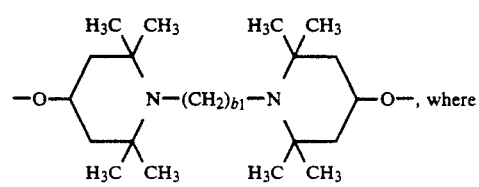

b$_1$ is 2 to 6, or

A is —O—CH$_2$—CH=CH—CH$_2$—O—, —O—CH$_2$—C≡C—CH$_2$—O—,

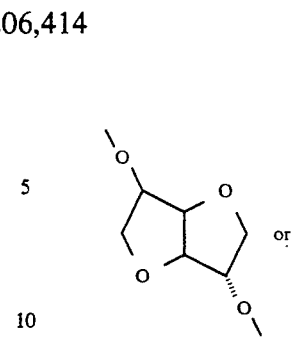

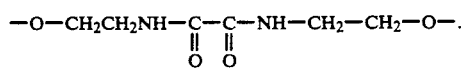

The process of the invention is particularly preferred for the preparation of a compound of the formula VII in which:
if n=1:
A is —OR$_4$, where
R$_4$ is C$_2$-C$_{18}$alkyl,
or for the preparation of a compound of the formula III in which:
if n=2:
A is —O—C$_x$H$_{2x}$—O—, where
x is 2 to 6,
A is —O—(CH$_2$—CH$_2$—O)$_a$—CH$_2$—CH$_2$—O— where
a is 1,2 or 3, or
A is —O—CH$_2$—CH$_2$—B—CH$_2$—CH$_2$—O— where
B is —S— or

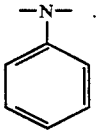

Particularly preferred processes are those for the preparation of a compound of the formula VII in which n=1 or 2.

Further preferred processes are those for the preparation of a compound of the formula VII in which
R$_4$ is hydrogen,
if n=3:
A is

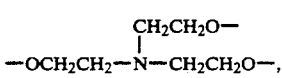

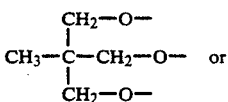

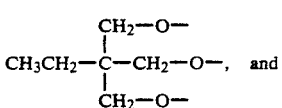

if n=4:
A is

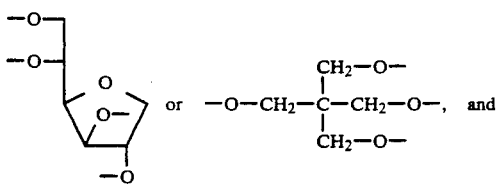

if n=6:
A is

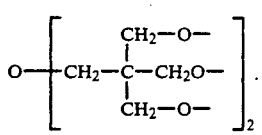

The process according to the invention is very particularly preferred for the preparation of a compound of the type:

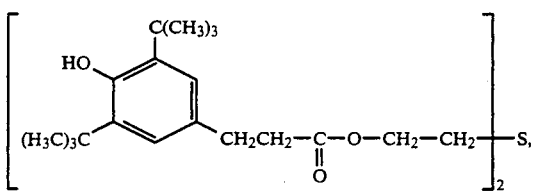

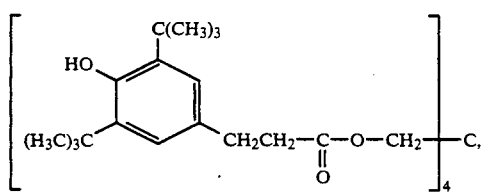

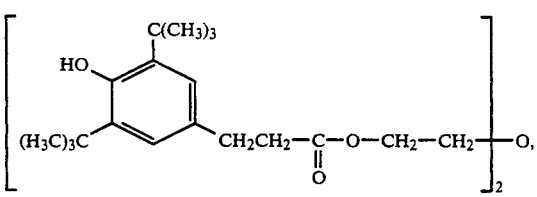

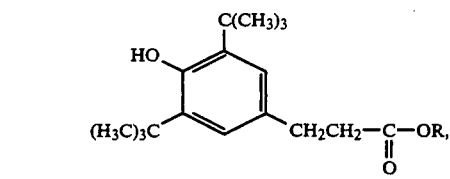

where R is $C_2-C_{18}$alkyl, in particular $C_{18}H_{37}$alkyl.

The process is expediently carried out by reacting the reaction mixture from the first step, generally still dissolved in the same solvent or in the melt, with the compound of the formula III without isolating the intermediates.

The process is not sensitive per se to the pressure used, and is therefore preferably carried out at atmospheric pressure, under reduced pressure or in a high vacuum.

The catalyst from the first step may be in the reaction mixture in the second step, and it is also possible to additionally add a further catalyst, as mentioned above, to the reaction mixture.

The catalyst should be present in the reaction mixture in the second step in, for example, amounts from 0.1 to 10 mol-%, expediently from 1 to 5 mol-% and preferably from 2 to 4 mol-%, of active material, based on the compounds of the formula V.

The ratio between the compound of the formula V and the compound of the formula III in the reaction mixture is not crucial and can be, for example, from 0.8 to 1.3 mol of the compound of the formula V per equivalent of the compound III. From 0.95 to 1.2 mol of the compound of the formula V per equivalent of the compound III and preferably from 1.0 to 1.05 mol of the compound of the formula V per equivalent of the compound III are expedient.

The reaction temperature in the second step may be, for example, between 110° and 240° C., expediently between 130° and 195° C. and preferably between 135° and 190° C.

The reaction in the second step of a compound of the formula V with a compound of the formula III generally takes between 1 and 5 hours, expediently between 1 and 4 hours and preferably between 1 and 3 hours, until optimum yields are achieved.

In the second step too, the catalyst may be suspended in the reaction mixture, for example in powder form or broken into pieces. It is also possible to carry out the process using the catalyst in a fixed bed.

When the second reaction step is complete, the catalyst, if in suspension, can be separated off, for example filtered off, and the end product can be isolated by measures known per se, for example crystallisation from a solvent, such as methanol, isopropanol, a methanol/water mixture, an isopropanol/water mixture, benzene, toluene, xylene, ligroin, n-hexane, etc.

If necessary, the reaction mixture and/or the end product from the second step can be neutralised using an acid, for example formic acid, acetic acid, sulfuric acid, hydrochloric acid, etc.

The compounds of the formula VII prepared according to the invention are, for example, valuable antioxidants against oxidative, thermal or actinic degradation of sensitive organic materials. Examples of such materials are synthetic polymers or functional fluids, such as lubricants, hydraulic fluids or metalworking fluids, etc.

The examples below illustrate the invention in further detail. All percentages or parts are by weight, unless stated otherwise.

EXAMPLE 1

Preparation of a Catalyst

Very pure calcium oxide having a ballast content of Fe<10 ppm, Cu<10 ppm, heavy metals (for example Pb) <10 ppm each, <40 ppm in total, oxygen-transferring anions, for example $AsO_4^{3-}$ and $NO_3^-$, and peroxides <100 ppm each, <200 ppm in total, acidic anions, for example $SO_4^{2-}$ and $Cl^-$, <500 ppm each, <1000 ppm in total, is ground.

Since this raw material has a relatively high carbonate content, it is calcined at 1100° C. before further processing until the $CO_3^{2-}$ content has dropped to 0.1% by weight (maximum of 5 hours).

All operations (including the calcining) are carried out under an inert gas ($N_2$) or in vacuo.

A sealable stainless-steel kneader equipped with temperature-control jacket and discharge device is charged with 200–300 ml of freshly distilled water (without $CO_2$). The kneader is flushed with $N_2$, and 100 g of the ignited calcium oxide is introduced in portions (the temperature must not exceed 80° C.) into the water with effective kneading. When the reaction is complete, a solution of 16.7 g of potassium fluoride in 20 ml of distilled water is poured into the suspension. After kneading, but before the paste begins to become viscous, it is discharged onto a Teflon-coated steel sheet. The catalyst prepared in this way is dried in vacuo under a stream of nitrogen ($N_2$) by heating to 160° C. for 5 hours. The dried catalyst has a stoneware-like appearance and is in the form of sheets. The material is then broken up and comminuted to a grain size of 0.2–0.5 mm. The catalyst is stored under an inert gas ($N_2$) until used. The catalyst contains 10% by weight of K (calculated as anhydrous catalyst), less than 100 ppm of active oxygen and less than 1% of $CO_3^{2-}$.

EXAMPLE 2

5 g of the catalyst as in Example 1 and 43.8 g of pentaerythritol are added to 376.4 g of methyl β-(3,5-di-tert-butyl-4-hydroxyphenyl)propionate, and the reaction temperature is increased in steps to 190° C. while simultaneously applying a vacuum of less than 1000 Pa. The transesterification is complete after 4 hours. The reaction mixture is filtered while hot, the readily volatile components are removed from the filtrate by distillation, and the residue is recrystallised from methanol. The conversion is about 94%, based on the starting materials, and the product is pentaerythritol tetrakis[3-(3,5-di-tert-butyl-4-hydroxyphenyl)propionate] of the formula

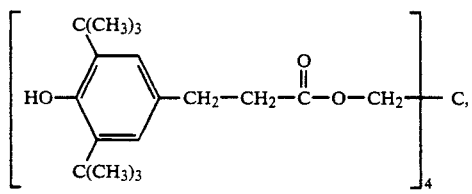

having a melting point of 118° C.

EXAMPLE 3

Preparation of methyl (3,5-di-tert-butyl-4-hydroxyphenyl)propionate 103.2 g (0.5 mol) of 2,6-di-tert-butylphenol and 47.3 g (0.55 mol) of methyl acrylate are reacted in the presence of 5.8 g (2 mol-%) based on KF and phenol) of the catalyst from Example 1. The 2,6-di-tert-butylphenol and the catalyst are introduced into the reaction vessel, which is then evacuated. The reaction vessel is warmed to 65° C. until the 2,6-di-tert-butylphenol has melted. The melt is kept under vacuum and heated to 115° C. with stirring. At this temperature, the methyl acrylate is added dropwise over the course of 2 hours. The reaction mixture is then allowed to react to completion for 2 hours under a nitrogen atmosphere. The catalyst is filtered off, and the filtrate is subjected to fractional distillation in a high vacuum (124°–128° C./$10^{-2}$ mm Hg).

128.6 g, corresponding to 88% of theory, of virtually white crystals containing 99.7% of methyl (3,5-di-tert-butyl-4-hydroxyphenyl)propionate are obtained.

EXAMPLE 4

Reaction of 2,6-di-tert-butylphenol with methyl acrylate to give methyl β-(3,5-di-tert-butyl-4-hydroxyphenyl)propionate and subsequent transesterification using pentaerythritol to give pentaerythrityl tetrakis[β-(3,5-di-tert-butyl-4-hydroxyphenyl)propionate].

144.4 g (0.7 mol) of 2,6-di-tert-butylphenol and 7.7 g (2 mol-%) of a supported catalyst comprising 10% by weight of KOH on ignited and hydrated CaO as support are introduced into a flask, which is then flushed with nitrogen, and heated to 60° C. The slightly yellowish melt is stirred, and the temperature is increased to 115°–120° C. under a water-pump vacuum and maintained for 1 hour. The vacuum is released, and 66.3 g (0.77 mol) of methyl acrylate are added dropwise to the reaction mixture over the course of 2 hours. During the exothermic reaction, an excess pressure develops, which can escape through a condenser. The mixture is allowed to react to completion for a further hour at atmospheric pressure under a blanket of $N_2$.

A check by gas chromatography gives a yield of 98%.

18.4 g (0.135 mol) of pentaerythritol are added to the resultant reaction mixture, the reaction vessel is evacuated, and the temperature is increased to 190° C. over the course of 1½ hours, during which about 16 g of methanol are removed. The mixture is allowed to react to completion at 190° C. for a further 2 hours, and the melt at 190° C. is then filtered with suction. The melt is heated to 220° C. in a high vacuum, during which unreacted methyl β-(3,5-di-tert-butyl-4-hydroxyphenyl)propionate is distilled off. The residue is recrystallised from methanol, giving 146.3 g (92% of theory) of pentaerythrityl tetrakis-[β-(3,5-di-tert-butyl-4-hydroxyphenyl)propionate] as a white powder of melting point 118° C.

What is claimed is:

1. An improved process for the preparation of a compound of the general formula

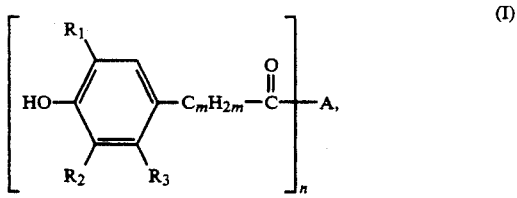

in which

R$_1$ and R$_2$ are identical or different and are hydrogen, C$_1$–C$_{18}$alkyl, phenyl, C$_1$–C$_4$alkyl-substituted phenyl, C$_7$–C$_9$phenylalkyl, C$_5$–C$_{12}$cycloalkyl or C$_1$–C$_4$alkyl-substituted C$_5$–C$_{12}$cycloalkyl, R$_3$ is hydrogen or methyl, m is 0, 1, 2 or 3, and n is 1, 2, 3, 4 or 6, where if n=1, A is —OR$_4$ in which R$_4$ is C$_2$–C$_{45}$alkyl, C$_5$–C$_{12}$cycloalkyl, C$_2$–C$_{18}$alkenyl,

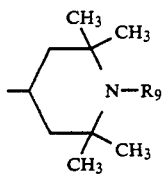

or —CH₂CH₂—XR$_{5a}$,

R$_9$ is hydrogen, C$_1$-C$_8$alkyl, C$_3$-C$_5$alkenyl, benzyl,

—O. or —OR$_{9'}$ in which
R$_{9'}$ is hydrogen, C$_1$-C$_{25}$alkyl or

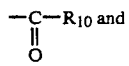

R$_{10}$ is hydrogen or C$_1$-C$_{20}$alkyl,
X is —O—, —S— or

R$_{5a}$ is

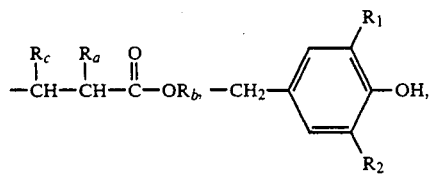

hydrogen, C$_1$-C$_{24}$alkyl, phenyl, C$_5$-C$_{12}$cycloalkyl or

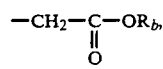

in which
R$_a$ is hydrogen or methyl,
R$_b$ is hydrogen or C$_1$-C$_{24}$alkyl and
R$_c$ is hydrogen or methyl with the proviso that R$_a$ and R$_c$ are not simultaneously methyl, and
R$_{6a}$ is C$_1$-C$_{18}$alkyl, phenyl, phenyl which is substituted by one or more alkyl groups having a total of 1 to 24 carbon atoms, or is C$_5$-C$_8$cycloalkyl, or, if n=2,
A is —O—C$_x$H$_{2x}$—O—, —O—(CH₂CH₂O)$_a$CH₂CH₂O—, —O—CH₂—CH₂—B—CH₂CH₂O—,

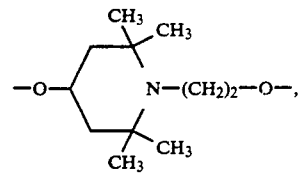

-continued

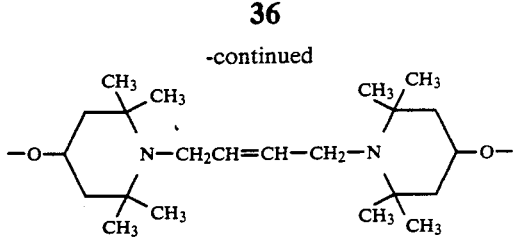

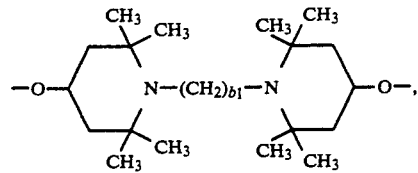

—O—CH₂CH=CHCH₂—O—, —O—CH₂C≡CCH₂—O—,

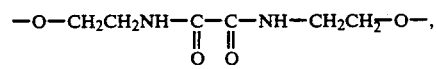

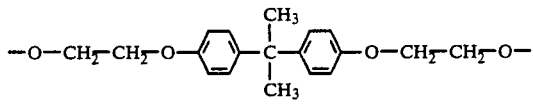

or

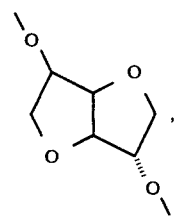

in which
a is a number from 1 to 30 and
x is a number from 2 to 20,
B is —S—,

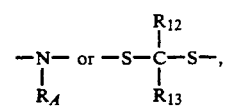

in which
R$_A$ is C$_1$-C$_{20}$alkyl, phenyl, phenyl which is substituted by one or more alkyl groups having a total of 1 to 20 carbon atoms, or is cyclohexyl or

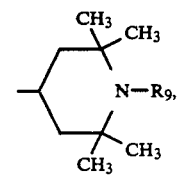

in which R$_9$ is as defined above, and
R$_{12}$ and R$_{13}$, independently of one another, are hydrogen, C$_1$-C$_{12}$alkyl or phenyl, or $R_{12}$ and $R_{13}$, together with the carbon atoms to which they are bonded, form a cycloalkyl ring having 5 to 12 carbon atoms, and $b_1$ is a number from 2 to 10, or, if n=3, A is

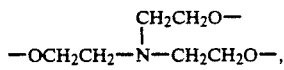

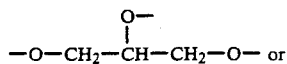

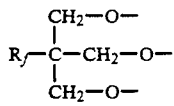

in which $R_f$ is $C_1$-$C_{24}$alkyl or phenyl, or if n=4,

A is

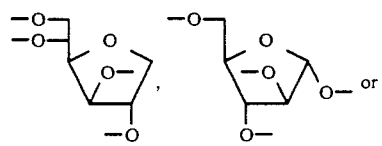

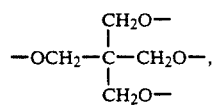

if n=6,

A is

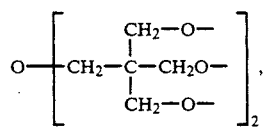

by reacting a compound of the formula II

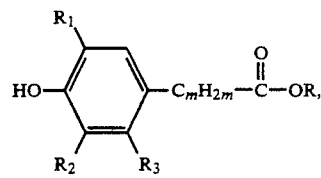

(II)

where m, $R_1$, $R_2$ and $R_3$ are as defined above, and R is alkyl having 1 to 4 carbon atoms, with a compound of the formula II $$A\mathrm{+H})_n, \qquad \text{(III)}$$

where A and n are as defined above, which improvement comprises carrying out the reaction in the presence of a catalyst which contains, as active material, an alkali metal compound of the formula IV $$M_mAn \qquad \text{(IV)}$$

in which

M is Li, Na, K, Rb or Cs, m is the valency of An and

An is a fluoride, hydroxide, phosphate, formate, acetate or —$OR_5$ radical, and $R_5$ is $C_1$-$C_4$alkyl or phenyl, and, as support, an alkaline material which, measured in 10% strength by weight aqueous suspension, has a pH >10, selected from one or more groups of substances from the series consisting of the alkaline earth metal oxides, hydroxides, aluminates and silicates.

2. A process according to claim 1, wherein a compound of the general formula Ia

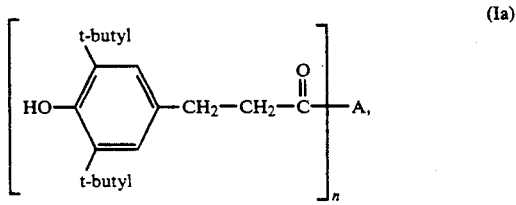

where A and n are as defined in claim 1, is prepared by reacting a compound of the formula IIa

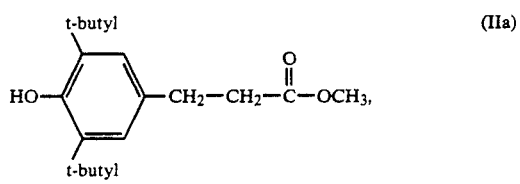

with a compound of the formula III according to claim 1 in the presence of a catalyst according to claim 1.

3. A process according to claim 1, wherein the catalyst contains an oxide, hydroxide, aluminate or silicate of the alkaline earth metals Mg, Ca, Sr and Ba, or a mixture thereof, as support.

4. A process according to claim 1, wherein the catalyst contains a hydroxide or fluoride of the alkali metals Na, K, Rb and Cs as the active material.

5. A process according to claim 1, wherein the catalyst contains from 0.15 to 30% by weight, calculated on the pure alkali metal and based on the anhydrous support, of active material.

6. An improved process for the preparation of a compound of the general formula V

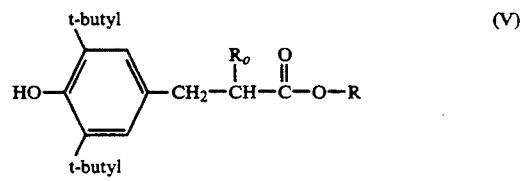

in which $R_o$ is hydrogen or $C_1$-$C_4$alkyl, and

R is $C_1$-$C_4$alkyl, reacting 2,6-di-tert-butylphenol with an acrylate of the formula VI

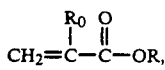  (VI)

in which $R_0$ and R are as defined above, which improvement comprises carrying out the reaction in the presence of a catalyst which contains, as active material, a component of the formula IV $$M_mAn \quad (IV)$$

in which
M is Na, K, Rb or Cs,
m is the valency of An and
An is a fluoride, hydroxide or —$OR_5$ radical, and $R_5$ is $C_1$-$C_4$alkyl or phenyl, and, as support, an alkaline material which, measured in 10% strength by weight aqueous suspension, has a pH >10, selected from one or more groups of substances from the series consisting of the hydrated alkaline earth metal oxides, aluminates and silicates.

7. A process according to claim 6, wherein the catalyst contains from 0.15 to 30% by weight, calculated as the pure alkali metal and based on the support, of active material.

8. A process according to claim 6, wherein the catalyst contains a support whose carbonate content is less than 0.1% by weight and whose iron content is less than 10 ppm.

9. A process according to claim 6, wherein the catalyst is used in an amount of from 0.1 to 10 mol-% of active material, based on 2,6-di-tert-butylphenol.

10. An improved process for the preparation of a compound of the general formula VII

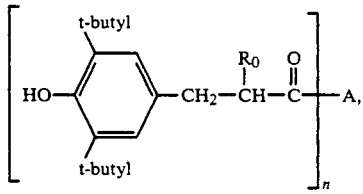  (VII)

in which
$R_0$ is hydrogen or $C_1$-$C_4$alkyl, and
n is 1, 2, 3, 4 or 6, and
if n=1,
A is —$OR_4$ in which
$R_4$ is $C_2$-$C_{45}$alkyl, $C_5$-$C_{12}$cycloalkyl, $C_2$-$C_{18}$alkenyl,

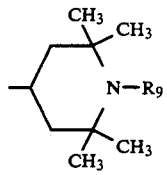

or —$CH_2CH_2$—$XR_{5a}$, in which
$R_9$ is hydrogen, $C_1$-$C_8$alkyl,

—O. or —$OR_{9'}$, in which,
$R_{9'}$ is hydrogen or $C_1$-$C_{25}$alkyl or

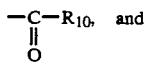 and $R_{10}$ is hydrogen or alkyl having 1 to 20 carbon atoms,
X is —O—, —S— or

$R_{5a}$ is

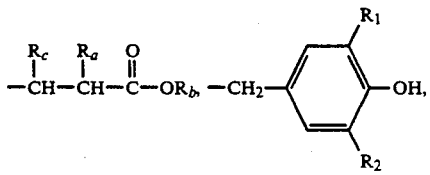

hydrogen, $C_1$-$C_{24}$alkyl, phenyl, $C_5$-$C_{12}$cycloalkyl or

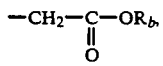

in which
$R_a$ is hydrogen or methyl,
$R_b$ is hydrogen or $C_1$-$C_{24}$alkyl and
$R_c$ is hydrogen or methyl, with the proviso that $R_a$ and $R_c$ are not simultaneously methyl, and
$R_{6a}$ is $C_1$-$C_{18}$alkyl, phenyl, phenyl which is substituted by one or more alkyl groups having a total of 1 to 24 carbon atoms, or is $C_5$-$C_8$cycloalkyl, or,
if n=2,
A is —O—$C_xH_{2x}$—O—, —O—$(CH_2CH_2O)_aCH_2CH_2O$—, —O—$CH_2$—$CH_2$—B—$CH_2CH_2O$—,

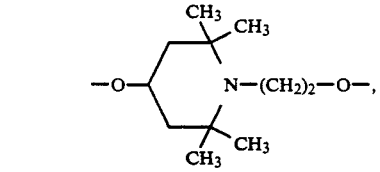

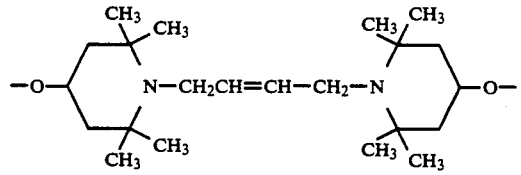

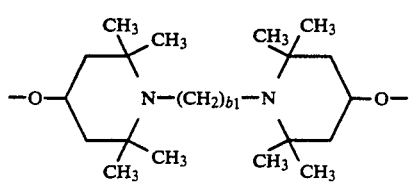

—O—$CH_2CH$=$CHCH_2$—O—, —O—$CH_2C$≡$CCH_2$—O—,

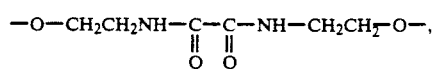

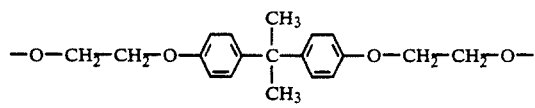

or

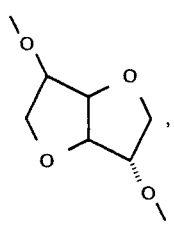

in which
a is a number from 1 to 30
x is a number from 2 to 20,
B is —S—,

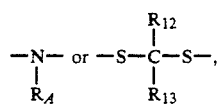

in which
$R_A$ is $C_1$–$C_{20}$alkyl having 1 to 20 carbon atoms, phenyl, phenyl which is substituted by one or more alkyl groups having a total of 1 to 20 carbon atoms, or is cyclohexyl or

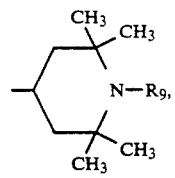

where $R_9$ is as defined above, and
$R_{12}$ and $R_{13}$, independently of one another, are hydrogen, $C_1$–$C_{12}$alkyl or phenyl, or
$R_{12}$ and $R_{13}$, together with the carbon atom to which they are bonded, form a cycloalkyl ring having 5 to 12 carbon atoms, and
$b_1$ is a number from 2 to 10, or
if n=3,
A is

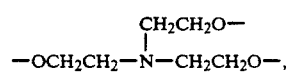

-continued

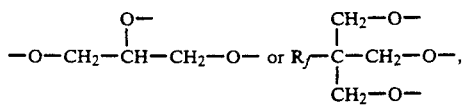

in which
$R_f$ is $C_1$–$C_{24}$alkyl or phenyl, or,
if n=4,
A is

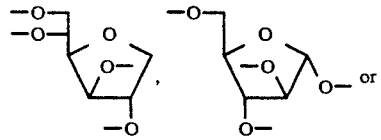

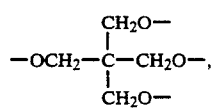

if n=6,
A is

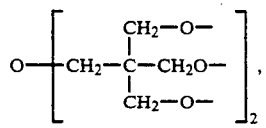

which improvement comprises reacting a compound of the formula VI

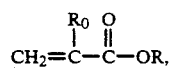           (VI)

in which $R_0$ is hydrogen or $C_1$–$C_4$alkyl and R is $C_1$–$C_4$alkyl, with 2,6-di-tert-butylphenol in a first step to give a compound of the formula V, and reacting the latter, without isolation from the reaction mixture, in a second step with a compound of the formula III

           (III)

where A and n are as defined above, both steps being carried out in the presence of a catalyst which contains, as active material, a component of the formula IV

           (IV)

in which
M is Na, K, Rb or Cs,
m is the valency of An and
An is a fluoride, hydroxide or —$OR_5$ radical, and $R_5$ is $C_1$–$C_4$alkyl or phenyl,
and, as support, an alkaline material which, measured in 10% strength by weight suspension, has a pH>10, selected from one or more groups of substances from the series consisting of the hydrated alkaline earth metal oxides, aluminates and silicates.

11. A process according to claim 6 where in the compound of formula V, $R_0$ is hydrogen or methyl.

12. A process according to claim 10 where in the compound of formula VII, $R_0$ is hydrogen or methyl.

* * * * *